United States Patent
Burke et al.

(10) Patent No.: US 7,587,927 B2
(45) Date of Patent: Sep. 15, 2009

(54) RAPID INTEGRITY TESTING OF POROUS MATERIALS

(75) Inventors: Aaron Burke, Hamilton, MA (US); George A. Gagne, Jr., Dracut, MA (US); Robert Wheeler, Billerica, MA (US)

(73) Assignee: Millipore Corporation, Billerica, MA (US)

( * ) Notice: Subject to any disclaimer, the term of this patent is extended or adjusted under 35 U.S.C. 154(b) by 93 days.

(21) Appl. No.: 11/599,501

(22) Filed: Nov. 14, 2006

(65) Prior Publication Data

US 2008/0110243 A1 May 15, 2008

(51) Int. Cl.
*G01N 15/08* (2006.01)
(52) U.S. Cl. .......................................... 73/38
(58) Field of Classification Search ..................... 73/38, 73/40

See application file for complete search history.

(56) References Cited

U.S. PATENT DOCUMENTS

| | | | |
|---|---|---|---|
| 3,973,928 A * | 8/1976 | Nierenberg et al. ............ 95/48 |
| 4,701,861 A | 10/1987 | Kauke ......................... 700/266 |
| 4,881,176 A | 11/1989 | Kononov ...................... 700/271 |
| 5,282,380 A | 2/1994 | DiLeo et al. .................... 73/38 |
| 5,457,986 A | 10/1995 | DiLeo et al. .................... 73/38 |
| 5,581,017 A | 12/1996 | Bejtlich, III .................... 73/38 |
| 6,568,282 B1 | 5/2003 | Ganzi ....................... 73/861.42 |
| 6,907,770 B2 | 6/2005 | Von Der Hardt et al. ........ 73/38 |
| 6,983,505 B2 | 1/2006 | McIntosh et al. ............... 7/129 |
| 2007/0089489 A1* | 4/2007 | Lewnard et al. ................ 73/38 |
| 2008/0105038 A1* | 5/2008 | Jons et al. ....................... 73/38 |

OTHER PUBLICATIONS

Phillips and DiLeo, 1996, *Biologicals* 24:243.
Badenhop; Meltzer and Jorritz, 1998, *Filtration in the Biopharmaceutical Industry*, Marcel Dekkar, Inc., New York, N.Y.
R. Prud'homme, T. Chapman, and J. Bowen, 1986, *Applied Scientific Research*, 43:67, 1986.

* cited by examiner

*Primary Examiner*—Hezron Williams
*Assistant Examiner*—Tamiko D Bellamy

(57) ABSTRACT

The invention relates to a rapid recirculation based integrity testing of porous material and to an apparatus and system for performing the same.

18 Claims, 11 Drawing Sheets

RAPID INTEGRITY TESTING OF POROUS MATERIALS

DESCRIPTION OF THE INVENTION

1. Field of the Invention

The invention relates generally to the field of validation testing. In specific embodiments the invention relates to integrity testing of porous materials.

2. Background of the Invention

Porous materials play a significant role in a wide variety of industrial applications including processing, e.g. filtering, packaging, containing, and transporting manufactured goods and raw materials. The industrial settings in which they are used include the pharmaceutical and biotechnology industries; the oil and gas industries and the food processing and packaging industries, to name but a few.

In several of these industries such as the pharmaceutical and biotechnology industries and the food processing industry porous materials, e.g. membranes, may be used as filtration devices to eliminate undesirable and potentially harmful contaminants from marketable end products. Quality control and quality assurance requires that these filtration devices comply with desired performance criteria. Integrity testing provides a means for ensuring that a particular device meets its desired performance criteria. Typically, in the case of membranes, integrity testing ensures that the membrane is free of defects, e.g. breaches in the membrane exceeding a desired size limitation, which would impair the membrane function and thus allow the end product to become contaminated with harmful or undesirable material.

A variety of integrity tests suitable for ensuring the performance criteria of membranes, e.g., filtration devices, have been previously described. These include the particle challenge test, the liquid-liquid porometry test, bubble point test, the air-water diffusion test and diffusion tests measuring tracer components (see, e.g., U.S. Pat. Nos. 6,983,505; 6,568,282; 5,457,986; 5,282,380; 5,581,017; Phillips and Dileo, 1996, *Biologicals* 24:243; Knight and Badenhop, 1990, 8th *Annual Membrane Planning Conference*, Newton, Mass.; Badenhop; Meltzer and Jorritz, 1998, *Filtration in the Biopharmaceutical Industry*, Marcel Dekkar, Inc., New York, N.Y.). A number of devices suitable for testing the integrity of a membrane have also been described (see, e.g., U.S. Pat. Nos.: 4,701,861; 6,907,770; 4,881,176).

The previously described integrity tests have significant shortcomings. The particle challenge test, for example, is destructive and thus can only be performed once on a given specimen. Although it can be used for post-use integrity testing, it is not suitable for pre-use validation, except for validating the performance of a production lot. Lot validation, however, provides little assurance regarding the integrity of individual membranes within a production lot. Moreover, the test procedures and analysis can be difficult and complex.

Flow based tests provide one method of integrity testing porous materials that does not require the destruction of the sample. This allows for the repeated testing of individual samples. Testing may be conducted prior to use or after one or more uses. Flow based tests may, however, be limited in their sensitivity, e.g. size detection limit of membrane defects. A further limitation of certain flow based tests is their reliance on detection methods which may be unduly cumbersome. Moreover, some flow based tests require the system to equilibrate to a steady state before integrity testing may begin. These tests are relatively slow and inefficient in their consumption of expensive and environmentally unfriendly reagents.

A need therefore exists for an integrity test that is suitable for any porous material, including, for example, both single layered and multi-layered devices, e.g. devices comprised of membranes. The test should be fast, sensitive, non-destructive, inexpensive and easy to execute. Moreover, the test should minimize the use of expensive reagents. It would also be useful to be able to characterize a defect, e.g. by size or density, to determine if a desired performance criteria of the porous material has been compromised as a result of the defect or if the defect is inconsequential in terms of performance criteria. A need also exists for an apparatus and system which can implement such a test. Various embodiments of the invention disclosed herein meet these requirements.

SUMMARY OF THE INVENTION

Certain embodiments of the invention provide a method, for evaluating the integrity of a porous material that is fast, sensitive, reproducible, non-destructive, inexpensive, flexible in terms of the orientation of the porous material, amenable to a wide variety of signal detection means and easy to execute. The porous material may comprise a single layered or multi-layered membrane device. Thus in some embodiments the invention provides a method of integrity testing of porous materials that is based on the concentration of one or more detectable substances, e.g. one or more gases, in the permeate of a porous material, such as a membrane. In certain embodiments the test may be a binary gas test, i.e. dependent on two gases, however, more than 2 gases are contemplated as are other detectable substances, e.g., one or more liquids. Other embodiments of the invention provide a method for characterizing a defect in a porous material, e.g. by size or density, to determine if a desired performance criteria of the porous material has been compromised as a result of the defect or if the defect is inconsequential in terms of performance criteria. Still other embodiments provide an apparatus and system which can implement these integrity tests.

In one embodiment the invention provides a method of assessing the integrity of a porous material comprising a) wetting the porous material with a liquid; b) contacting a first surface of porous material with a mixture comprising a carrier and a detectable substance; c) applying pressure to the first surface of the porous material such that at least some of the carrier and the detectable substance permeate the porous material; d) recirculating the mixture of b) from a permeate of the porous material in a fixed volume on the permeate side while continuing to apply the pressure of c); e) assessing the concentration of the detectable substance in the permeate of the porous material in a fixed volume over time. The test may optionally comprise an additional step f) comparing the assessed concentration in e) with the concentration of the detectable substance in a permeate of an integral porous material, wherein an assessed concentration in e) which is greater than the concentration of the detectable substance in a permeate of the integral porous material indicates the porous material is not integral. Integral, when referring herein to a porous material, means non-defective.

In another embodiment the invention provides a method of assessing the integrity of a porous membrane comprising a) wetting the porous material with a liquid b) contacting a first surface of the porous material with compressed air; and with a fluoro-carbon such that a mixture is formed comprising the compressed air and the fluoro-carbon ; c) applying pressure to the first surface of the porous material such that at least some of the carrier and the detectable substance permeate the porous material; d) recirculating the mixture of b) from a permeate of the porous material in a fixed volume on the permeate side while continuing to apply the pressure of c); e) assessing the concentration of the fluorocarbon in the permeate of the porous material over time; and f) comparing the assessed concentration in e) with the concentration of the fluoro-carbon in a permeate of an integral porous material submitted to the same conditions over time, wherein an assessed concentration in e) which is greater than the concentration of the fluorocarbon in a permeate of the integral porous material indicates the porous material is not integral.

In still another embodiment the invention provides a method of assessing the size of a defect in a sample porous material comprising a) wetting the porous material with a liquid; b) contacting a first surface of porous material with a mixture comprising a carrier and a detectable substance; c) applying pressure to the first surface of the porous material such that at least some of the carrier and the detectable substance permeates the porous material; d) recirculating the carrier and detectable substance found in a permeate of the porous material in a fixed volume on the permeate side while continuing to apply the pressure of (c); e) assessing the concentration of the detectable substance in the permeate of the porous material over time; and f) comparing the assessed concentration in e) with the concentration over time of the detectable substance in a permeate of one or more standard porous materials, wherein each of said one or more standard porous materials comprises a defect of known size and is submitted to the same test conditions as the sample porous material, thereby determining the size of the defect.

In a further embodiment the invention provides a method of characterizing a defect in a sample porous material comprising a) wetting the porous material with a liquid; b) contacting a first surface of porous material with a mixture comprising a carrier and a detectable substance; c) applying pressure to the first surface of the porous material such that at least some of the carrier and the detectable substance permeates the porous material; d) recirculating the carrier and detectable substance found in a permeate of the porous material in a fixed volume on the permeate side while continuing to apply the pressure of (c); e) assessing the concentration of the detectable substance in the permeate of the porous material over time; and f) comparing the assessed concentration in e) with a calculated theoretical concentration of the detectable substance in the permeate of one or more known standard porous materials comprising a defect of a predetermined size.

The skilled artisan will understand that one or more of the steps recited in each of the methods described above may be combined into a single step.

In yet another embodiment the invention provides an apparatus for assessing the integrity of a sample porous material comprising a) a housing suitable for receiving a porous material to be integrity tested; b) a source of a detectable substance in fluid communication with the housing; c) a source of a carrier for the detectable substance in fluid communication with the housing; d) a detector for detecting the detectable substance; e) a recirculation pump in communication with the detector and the housing for containing the porous material; and f) a source of an external force.

In still other embodiments the invention provides a system for assessing the integrity of a sample porous material comprising an apparatus suitable for assessing the integrity of a porous material and a programmable logic controller suitable for receiving input from a user.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF THE EMBODIMENTS

Methods of the Invention

Figure 1A:
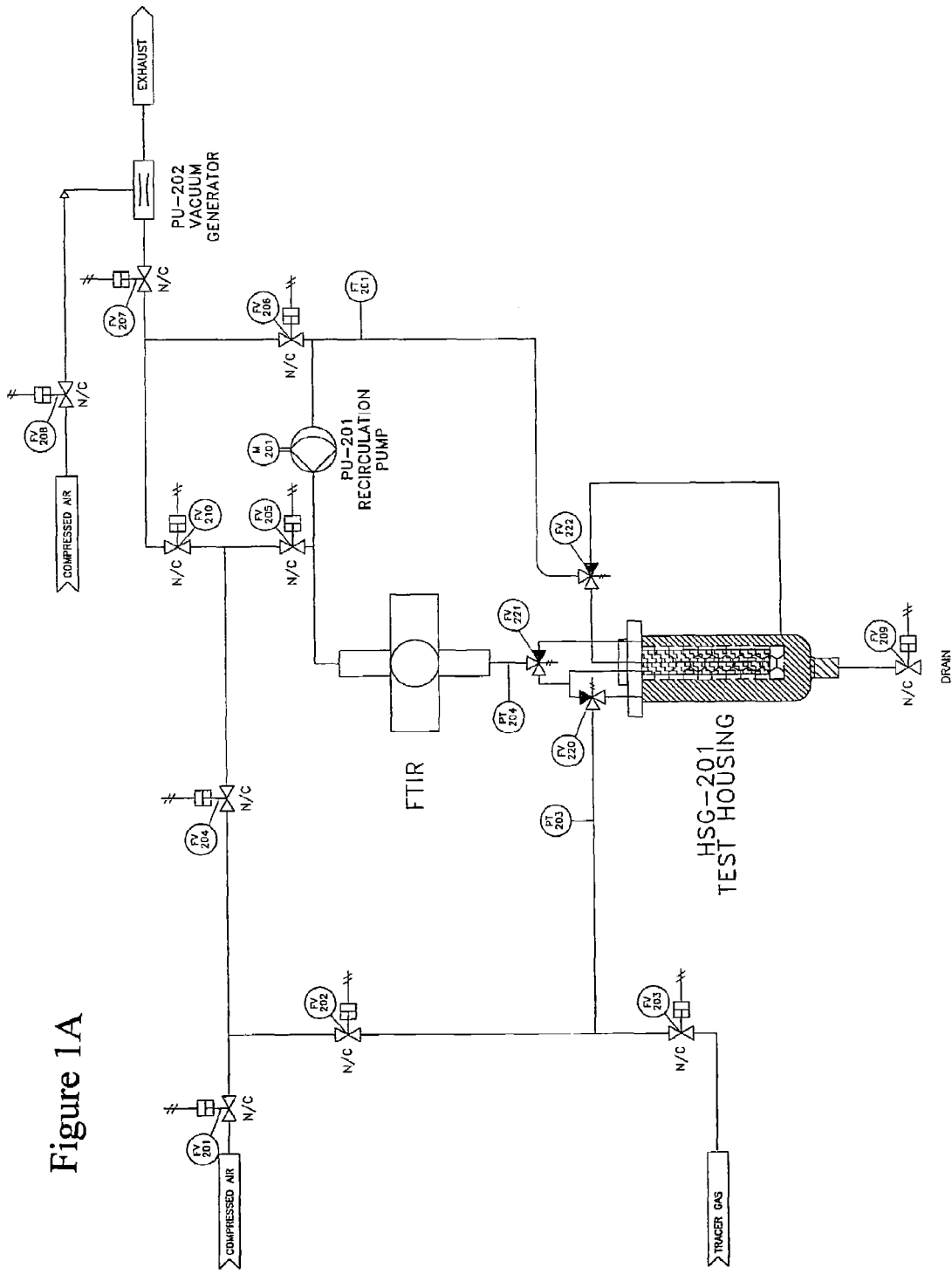
FIG. 1a is a schematic of an apparatus used to test the integrity of membrane cartridges according to one embodiment of the invention.

Certain embodiments of the invention provide a method, for assessing the integrity of a porous material. Typically the downstream side volume or permeate volume may remain relatively invariant. Moreover if the downstream volume is known and the diffusional flow through an integral membrane is known, or insignificant compared to the defect flow, the effective defect size may be determined from the rate of rise of the concentration of the detectable substance in the permeate. The test thus relies on measuring the concentration of at least one detectable substance, such as a gas or vapor in the permeate of a porous material as a function of time and then correlating that concentration with a known or predetermined value for an integral porous material such as a membrane and or alternatively for a porous material having a defect of known size, e.g. diameter. The detectable substance may be recirculated to present a uniform permeate sample to the detector. Recirculation may be accomplished using a pump in communication with the permeate side of the porous material being tested for integrity. In certain embodiments the benefits of recirculation may be both economical and environmental in that it limits amount of reagents used. The recirculation rate may be adjusted such that the detectable substance is quickly incorporated into the stream flowing to the detector. Recirculation eliminates the need to achieve a steady state and thus may provide a more rapid result compared to previously described integrity tests. Moreover, the method may be easily adapted to accommodate virtually any type of detector known in the art and thus in certain embodiments the invention may avoid the use of cumbersome detection means requiring a direct line of sight, e.g., a photo acoustic detector. The method may allow for detection of smaller defects compared to previously described techniques. The method is highly reproducible and in embodiments where the porous material is a membrane, the method permits testing the integrity of a membrane in any orientation. Thus, for example, an asymmetric membrane may be contacted with the mixture of the carrier and the detectable substance either from the tight surface where pore size is smaller, or the open surface where pore size is larger. Similarly the permeate which is fed to the detector may come from either side of the membrane, so long as it is opposite the side initially contacted with the mixture. Thus a membrane may be integrity tested from either orientation without the need to physically reorient the membrane. Both sides of the porous material being tested may be evacuated by means of one or more exhaust conduits in fluid communication with each side of the porous material thus facilitating removal of the detectable substance after each test thereby reducing background of subsequent tests and increasing sensitivity.

The steady state diffusion equation provides a flow rate that is the maximum that would be seen if the integrity test described herein was allowed to equilibrate to steady state. This suggests why a transient test time, which may be performed quickly, may be well suited for determining the integrity of porous materials being tested. If the system reaches steady state, diffusion may overcome the convective flow through the defect making detection of the detectable substance difficult if not impossible.

Steady State Gas Diffusion Equation (Fick's First Law)

$$Q = \frac{\rho_L}{M_L} \frac{D}{H} \frac{(P_{in} - P_{out})}{L} \frac{RTA_f\varepsilon}{P_{out}}$$

where:
Q=Gas flow (cm$^3$/sec) evaluated at downstream conditions
$\rho_L$=Liquid density (g/cm$^3$)
$M_L$=Liquid molecular weight (g/mol)
D=Diffusivity of the gas through the liquid (cm$^2$/sec)
H=Henry's law constant (psi)
$P_{in}$=Absolute upstream pressure (psia)
$P_{out}$=Absolute downstream pressure (psia)
L=Membrane thickness (cm)
R=Gas constant (1205.95 cm$^3$ psi/mol/K)
T=Absolute temperature (K)
$A_f$=Total membrane frontal area (cm$^2$)
$\varepsilon$=Membrane porosity Choke flow, which is applicable to a transient test time is described infra at page 16. In certain embodiments the integrity test according to the invention may be practiced without the necessity of allowing the system to reach steady state, and thus provides for a rapid determination regarding the integrity of a porous material such as a membrane.

The conditions under which the methods of the invention are practiced may be chosen by the skilled artisan. As an example, the methods of the invention may be practiced at a temperature ranging from about 0° C. to about 100° C., 4° C. to about 60° C., 10° C. to about 50° C., 15° C. to about 30° C. In one embodiment the invention is practiced at a temperature of about 20° C. In another embodiment the invention may be practiced at a temperature of about 4° C.

The test may be run under differential pressure that is one side of the sample porous material to be tested may be at a first pressure and a second side of the sample porous material may be at a second pressure. In certain embodiments at least one side of the porous material is at a pressure which may be equal to or near the bubble point of the porous material. Thus the pressure on the feed side of the sample porous material may be greater than the pressure on the permeate side of the porous material.

The methods of the invention may be practiced at a pressure, e.g., a feed pressure, ranging from about 1 PSI to about 100 PSI; from about 10 PSI to about 70 PSI; from about 5 PSI to about 60 PSI; from about 20 PSI to about 45 PSI. In another embodiment the methods of the invention may be practiced at a pressure of about 30-50PSI. In one embodiment the methods of the invention may be practiced at a pressure of about 50 PSI. In another embodiment the methods of the invention may be practiced at a pressure of about 30 PSI. In yet another embodiment the methods of the invention may be practiced at a pressure of about 15 PSI. In a further embodiment the invention may be practiced at a pressure that is just below the bubble point of the porous material. In still other embodiments the pressure may be ramped up, e.g., slowly increased by small increments while measuring flow rate and concentration. In yet other embodiments the pressure may be ramped down, e.g., slowly decreased by small increments while measuring flow rate and concentration. The pressure may be ramped up or down in stepwise increments. The stepwise increments can be between 0.5 psi and 100 psi; or between 1 psi and 25 psi; or preferably between 5 psi and 10 psi. In some embodiments the test may be run with at least one side of the sample porous material to be tested under vacuum, e.g. at a pressure less than 14.7 psia, less than 5 psia.

In certain embodiments both the carrier and the detectable substance may both be a gas. In these embodiments the sensitivity of the test may be as follows. The flux of tracer gas due to diffusion may be time dependent (and equal zero at time=0) while the convective flux may remain constant once a pressure gradient is established and maintained. Upon pressurizing the upstream side, of the membrane, the flux due to diffusion will be zero (but increasing) while the convective flux may be fully established. The limitations of sensitivity then become 1) the time required to present a representative sample to the detector, 2) the detector sensitivity, and 3) the delay before the diffusive flow becomes significant compared to the convective flow.

$$\frac{dy_{Tracer}}{dt} = \frac{n_{Tracer}|_{Diffusion} + n_{Tracer}|_{Convection}}{N_{Total}}$$

Where:

$y_{Tracer}$ = Permeate side Tracer gas mole (or volume) fraction $n_{Tracer}$ = molar flux of tracer (moles/second)

$N_{Total}$ = total amount of gas in the permeate side volume (moles)

In some embodiments a detectable substance, e.g., a tracer gas that reacts with a component of the wetting liquid may be used. For example, the porous material could be wet with an aqueous solution of sodium hydroxide. The porous material could be contacted with a mixture of carbon dioxide (detectable substance) and compressed air (carrier), such that any $CO_2$ which diffuses into the water would react. However, any gas which flows through a defect would not react, thus the presence of $CO_2$ on the permeate side would be indicative of a defect. The skilled artisan would understand that the byproducts of the reaction (which in this case are water soluble) would have to be flushed from the porous material before it is used.

1. Quantifying Defect Size

As discussed above, it may be desirable in certain situations to be able to characterize a defect or defects in a porous material beyond merely noting its presence or absence. Certain embodiments of the invention provide a method of calculating defect diameter and distribution density, both of which may be useful in assessing a material's integrity, particularly as it relates to retention. Gas flow through a defect is due to primarily to convective rather than diffusive transport. Several researchers have modeled gas flow in defects assuming the Hagen-Poiseuille equation applies. However, one skilled in the art will recognize that this equation is valid only at the limit of very low pressure differentials across the membrane (R. Prudhomme, T. Chapman, and J. Bowen, 1986, *Applied Scientific Research*, 43:67, 1986.). At typical integrity test conditions, the flow through a defect more closely follows choke flow, particularly if the defect diameter is large relative to the thickness of the retentive zone within the membrane. In general, the transition from Hagen-Poiseuille flow to turbulent flow to choke flow is a function of the ratio of the permeate pressure to the feed pressure. The choke flow equation is provided below and may be used to calculate the defect diameter assuming a single defect is present:

$$Q = \frac{\frac{N_p P_{in} \pi d_p^2}{4} \sqrt{\frac{\gamma M w}{RT} \left[\frac{2}{\gamma+1}\right]^{\frac{\gamma+1}{\gamma-1}}}}{\rho_{exit}}$$

$$\rho_{exit} = \frac{P_{out} M w}{RT}$$

where:
Q=Gas flow ($cm^3$/sec) evaluated at downstream conditions
$N_p$=Number of defects
$D_p$=Defect diameter (microns)
$\gamma$=Ratio of specific heats
Mw=Gas molecular weight (g/mole)
R=Gas constant (1205.95 $cm^3$ psi/mol/K or 8.314 E+7 g $cm^2/mol/K/s^2$)
T=Absolute Temperature (K)
$P_{in}$=Absolute upstream pressure (psia)
$P_{out}$=Absolute downstream pressure (psia)

Porous Materials

The integrity of any porous material may be assessed using the methods, devices and systems of the invention. As an example, but not as a limitation, the porous material may take the form of a cartridge, a cassette, a sheet, a column, a chip, a bead, a plate container, a bottle, a cap, a cylinder, a tube, a hose, or a monolith.

The porous material may be comprised of an organic or inorganic molecules or a combination of organic and inorganic molecules. The porous material may be comprised of a hydrophilic compound, a hydrophobic compound, an oleophobic compound, an oleophilic compound or any combination thereof. The porous material may be comprised of one or more a polymers or copolymers. The polymers may be crosslinked.

The porous material may be comprised of any suitable material, including, but not limited to polyether sulfone, polyamide, e.g., nylon, cellulose, polytetrafluoroethylene, polysulfone, polyester, polyvinylidene fluoride, polypropylene, a fluorocarbon, e.g. poly(tetrafluoroethylene-co-perfluoro(alkyl vinyl ether)), poly carbonate, polyethylene, glass fiber, polycarbonate, ceramic, and metals. The porous material may be in the form of a single or multilayered membrane. The porous material may be, for example, a hollow fiber, a tubular format, a flat plate, or spirally wound.

In certain embodiments the porous material may be a membrane, e.g., a filter or filtration device comprising a membrane. The porous material may be capable of excluding solutes based on the size of the solutes. As an example the pores of the material may be too small to allow the passage of a particle of a specific size, e.g., diameter or a particular molecular weight. The membrane may be contained in a housing e.g., a cartridge, a cylinder, a cassette. The membrane may be a flat sheet, a multi-layered sheet, a pleated sheet or any combination thereof. The membrane pore structure may be symmetric or asymmetric. The membrane may be used for filtration of unwanted materials including contaminants such as infectious organisms and viruses, as well as environmental toxins and pollutants. The membranes may include ultrafiltration membranes, microfiltration membranes, and reverse osmosis membranes.

Liquids and Wetting Agents

In certain embodiments the porous material may be wetted with one or more liquids prior to testing. The methods of the invention provide for the use of any suitable liquid to be used as a wetting agent for the porous material. Selection of a wetting agent is within the skill of the artisan and may be determined based on chemical and physical properties of the porous material. Porous materials vary in terms of their wettability, which is often expressed in terms of the contact angle θ. The methods of the invention, can be adapted for hydrophobic membranes, for example, by selecting non-aqueous solvents or prewetting it with low surface tension fluids (such as a mixture of 30% isopropyl alcohol and 70% water) and exchanging the low surface tension fluid with water or alternatively wetting the membrane with one or more organic solvents. The operating pressure can be adjusted by selecting fluids with the appropriate surface tension γ, which generally range from about 74 dyne/cm for water to about 10 dyne/cm for perfluorinated solvents. A skilled artisan will thus understand that a liquid may be selected by considering the chemical properties of the porous material to be tested. As an example, where the porous material is comprised of a hydrophilic material a suitable liquid includes water or a solution comprised of water. The solution may be, for example, aqueous solutions containing salts and oxygenated hydrocarbons such as aldehydes or alcohols or neat alcohols such as isopropyl alcohol. Where the porous material is a comprised of a hydrophobic material a suitable liquid may include any organic solvent such as dodecane, perfluorinated compounds, carbon tetrafluoride, hexane, acetone, benzene, toluene or the like.

Carriers and Detectable Substances

The carrier and the detectable substance may be chosen by the skilled artisan, based on the solubility of the detectable substance in the carrier. In some embodiments, it is contemplated that the detectable substance may be one or more vapors or liquids. In other embodiments the carrier and detectable substance may be a mixture of gases and vapors. In other embodiments the carrier and the detectable substance may both be gases. Virtually any gas composition may be used in practicing the methods of the invention, provided that the solubilties in the liquid used to wet the porous material are such that the detector is not flooded with the carrier thereby blinding the detector to the presence of the detectable substance. Typically, the mixture comprising the carrier and the detectable substance will have a higher concentration of carrier than detectable substance.

Where a plurality of gases is used, i.e., where the carrier and the detectable substance, or substances are all gases, the percentage of each gas in the mixture may be chosen by the skilled artisan. As an example, where 2 gases are used the first gas may be used at a percentage volume ranging from about 0.01% to about 99.99%, and the second gas may be present at a percentage volume ranging from about 0.01% to about 99.99%.

The invention provides for flexibility with regard to choices of liquid and gas components and compositions. Carriers and detectable substances will be chosen based upon their solubility in the liquid used to wet the porous material. There ratio of solubility of the carrier to the detectable substance may be readily determined by the skilled artisan and may range from about 500:1; about 250:1; about 100:1 about 80:1; about 60:1 about 50:1; about 40:1; about 30:1; about 20:1; about 10:1 about 5:1. If the ratio of solubility between the carrier and the detectable substance is too great, e.g. greater than 1000:1 the detector, may in some cases become flooded with carrier making the detection of the detectable substance difficult.

Suitable carriers include compressed air, nitrogen, oxygen, Noble gases, e.g., helium, neon, argon, krypton, xenon, radon, alkanes, e.g., methane, ethane, propane and the like. Suitable detectable substances may include fluoro carbons such as Freon, e.g. $C_2F_6$, alcohol, sulfur hexafluoride, helium, alkanes, e.g., methane, ethane propane etc., olefins, e.g. ethylene, propylene, butylenes etc., carbon dioxide, carbon monoxide, hydrogen, volatile organic liquid vapors, e.g., methanol, ethanol, acetone etc. The skilled artisan will appreciate that sensitivity of the integrity test will be influenced by the detector capability and the rate at which diffusion begins to occur.

In some embodiments, e.g., where the carrier and detectable substance are both gases, it is useful to choose gas pairs with moderate differences in permeability and gas compositions that have one species in trace concentration (i.e. the detectable substance) and the other present as the bulk species (i.e. the carrier). In the limit of using a dilute tracer gas, the sensitivity of the gas measurement is a function of the feed composition and (, the ratio of permeability of one gas (i) to another (j).

$$\Phi = \frac{D_i S_i}{D_j S_j}$$

For example, $\Phi$ can vary from approximately 0.001 to 1 for binary gas mixtures using common species such as nitrogen, oxygen, carbon dioxide, helium, hydrogen, and hexafluoroethane, with water as the pore-filling liquid. For tests where the wetting liquid is a hydrophobic liquid, such as dodecane, gas pairs could include high permeability gases such as ethane, propane, and butane paired with low-permeability gases such as helium, hydrogen, and nitrogen.

In some embodiments at least one of the gases is a hexafluoroethane. In other embodiments at least one of the gases is a noble gas. In still other embodiments at least one of the gases is $CO_2$. In further embodiments at least one of the gases is comprised of a mixture of gases, e.g. air. Where the gases are provided as a mixture of more than one gas, the mixture may be premixed before being contacted with the porous material. Wide ranges of gas composition are available; for example feed gas mixtures of hexafluoroethane in $CO_2$ can vary from less than 0.1% to more than 99.9%. The skilled artisan will be able to choose appropriate gases and gas mixtures based upon known properties such as solubility or permeability in the wetting liquid.

Apparatus and Systems

In certain embodiments the invention provides an apparatus suitable for determining the integrity of a porous material. An example of an apparatus suitable for use in the methods of the invention is shown in schematic form in FIG. 1a. The apparatus may comprise a) a housing suitable for receiving a porous material to be integrity tested; b) a source of a detectable substance in fluid communication with the housing; c) a source of a carrier for the detectable substance in fluid communication with the housing; d) a detector for detecting the detectable substance; e) a recirculation pump in communication with the detector and the housing for containing the porous material; and f) one or more sources of external force.

The detector may be any commercially available detector suitable for detecting the detectable substance, e.g., a tracer gas or vapor. The detector need not be custom made as required by previously described photo acoustic detection methods. The detector may be, for example, Fourier Transform Infra-Red Spectroscopy, mass spectroscopy, gas chromatography.

The external energy source may include any compressed gas, such as compressed nitrogen, compressed air. Alternatively the external energy source may include a vacuum pump or a combination of one or more sources of compressed air and one or more vacuum pumps. A combination of external energy sources, e.g. one or more pumps and one or more sources of compressed gas are also contemplated.

The apparatus may comprise one or more valves, e.g. two valves, three way valves and the like, to control the flow of the carrier and or the detectable substance, e.g. to the sample contained in the housing, to the detector, and or to the recirculation pump. One or more valves may also be used to control exposure of the sample to an external force. One or more valves may be used to control the flow of the carrier and detectable substance such that the porous material may be tested for integrity from more than one orientation. Thus where the test is performed on a membrane, valves may control the flow of the carrier and detectable substance such that the permeate is found on either the tight side of membrane or the open side of the membrane. Similarly embodiments of the invention contemplate detecting the permeate on either the skinned surface of the membrane or the skinless surface of the membrane.

Referring to FIG. 1a, the apparatus comprises a housing (201) for receiving a sample to be integrity tested, e.g. a membrane cartridge. The housing may comprise a head having one or more ports and a hollow tube which contacts the housing head and extends into the body of the housing in a direction running parallel to a housing wall. The hollow tube may be suitable for transporting gas into or out of the housing. The housing may be in fluid communication with a gas source (TK-201) and with a detector and a recirculation pump (PU-201). Positioned between the gas source and the housing, and between the housing and both the detector and the recirculation pump (PU-201) the apparatus may comprise one or more valves for controlling the flow of gas. The apparatus may comprise a series of three way valves (FV 220; FV 221, FV 222) which control the flow of gas into and out of the housing such that the sample membrane, e.g. a cartridge, may be integrity tested from either surface of the cartridge without the need to physically manipulate the sample membrane once it is positioned in the housing.

Figure 1B:
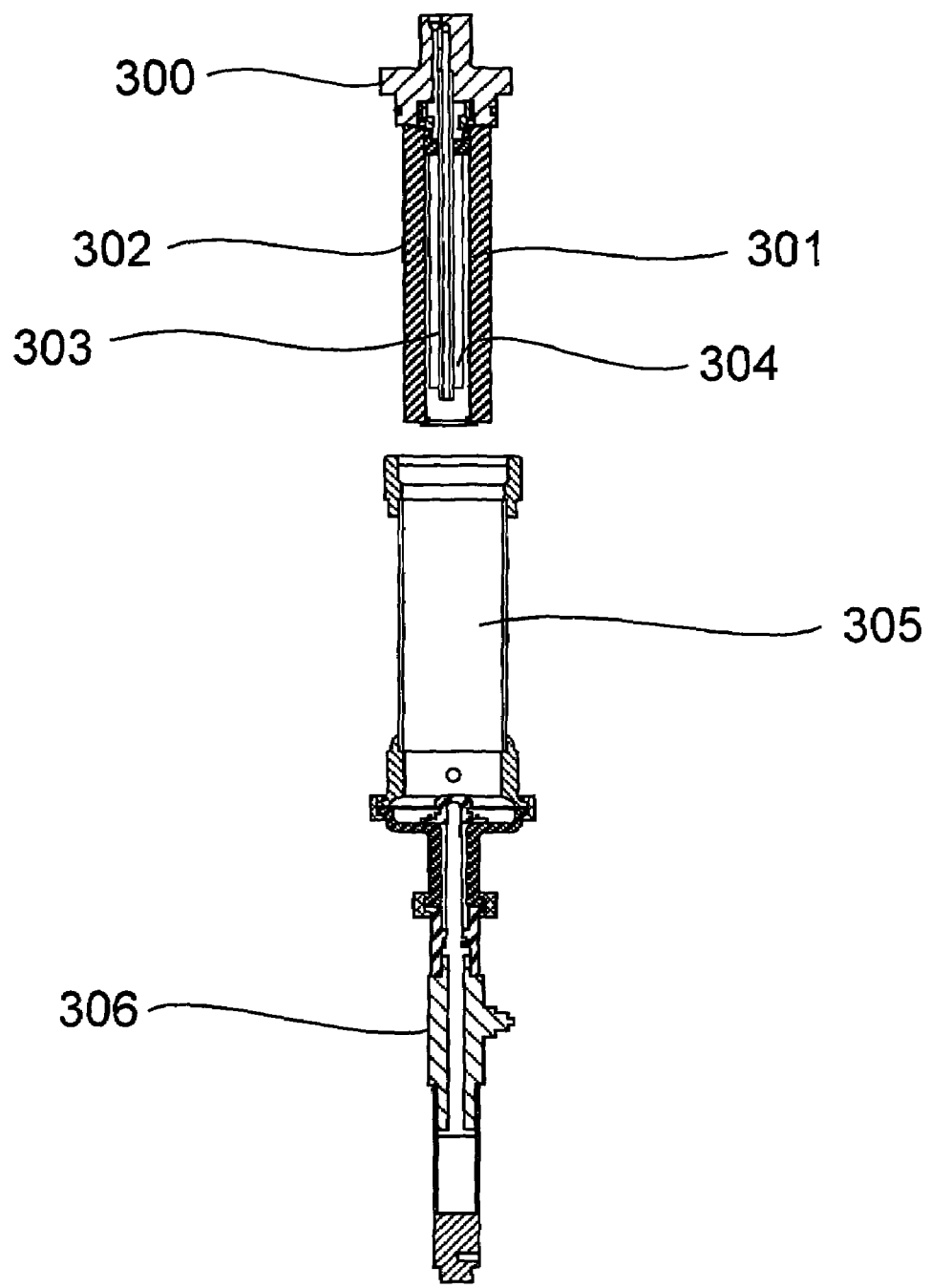
FIG. 1b is a first cross section of an apparatus housing and a sample membrane.

Referring to FIG. 1b, a cross section of a portion of the apparatus of FIG. 1a is shown including a housing head (300), a membrane cartridge interior support sleeve (301) extending from the housing head and suitable for receiving a sample membrane; a sample membrane for integrity testing (302); a hollow tube(303); a plastic filler 304 which may reduce the open interior volume of the housing thereby facilitating more rapid detection of the detectable substance, e.g. tracer gas; a housing bowl(305) suitable for receiving a sample membrane; a breaking cylinder(306) for holding the membrane sample in place.

Figure 1C:
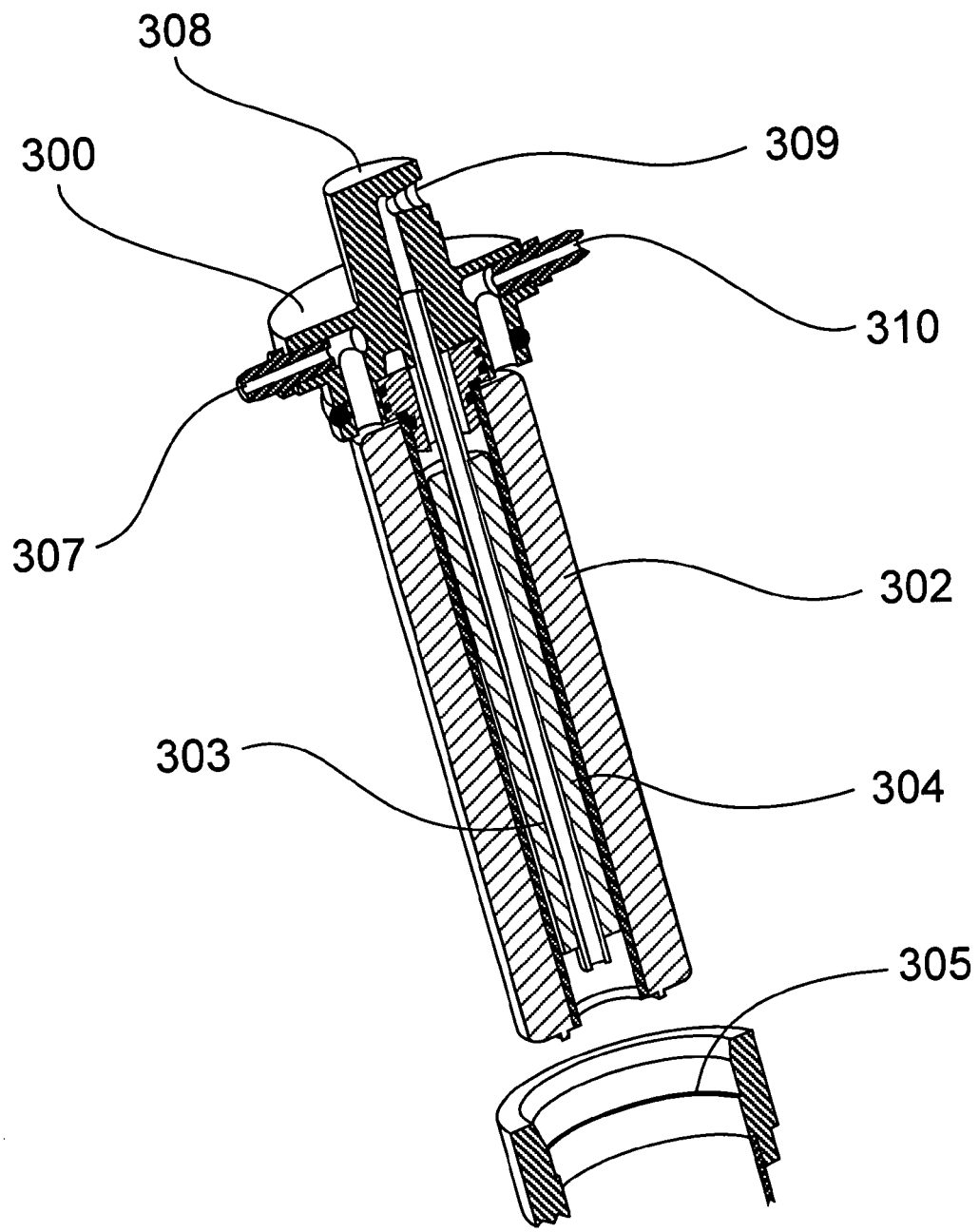
FIG. 1c is a second cross section of an apparatus housing and a sample membrane.
Figure 1D:
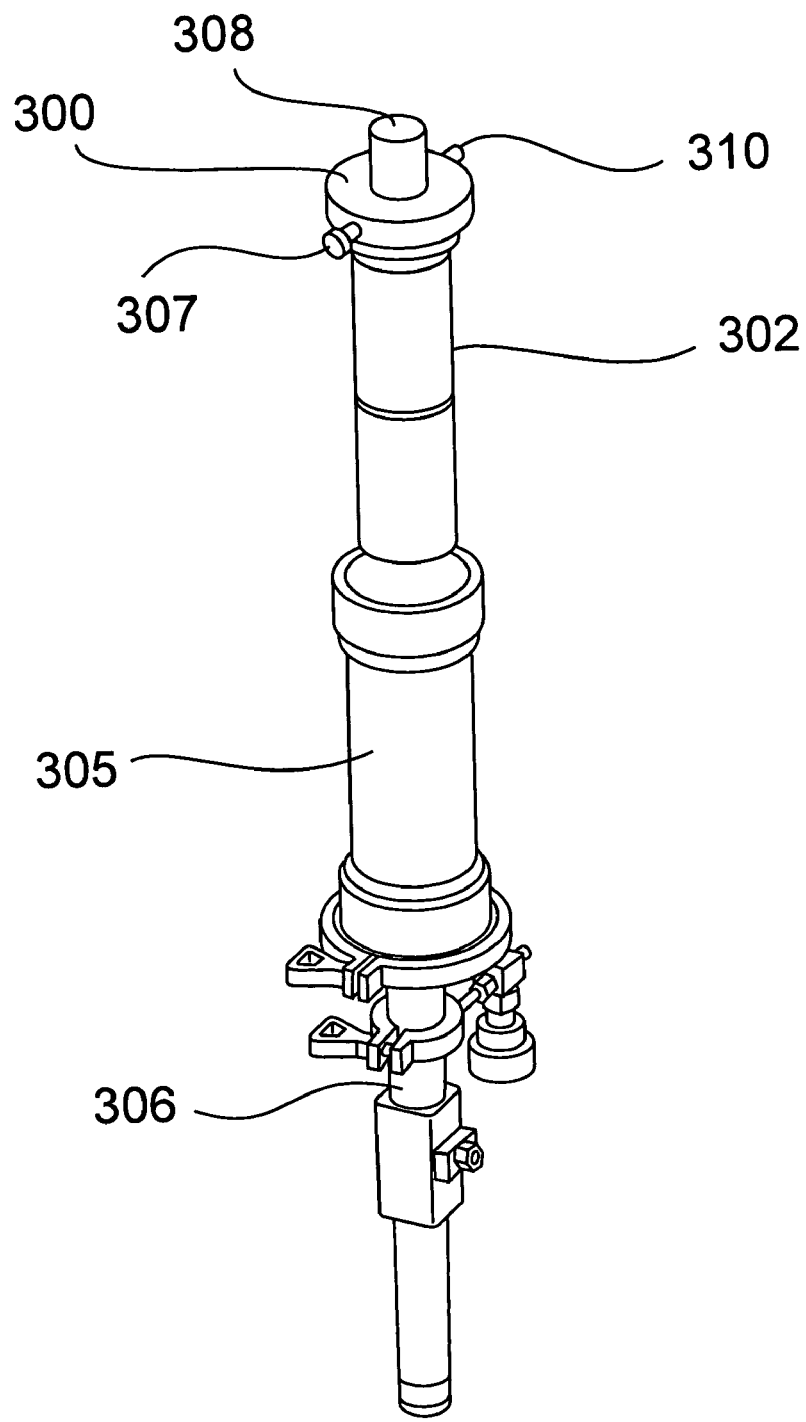
FIG. 1d is a side view of the housing and sample membrane.

FIG. 1c shows an alternate cross sectional view of the housing head, the membrane cartridge interior support sleeve and the housing frame. In this view four ports (307, 308, 309, and 310) are shown all of which serve to communicate with the exterior of the housing bowl and the interior of the membrane cartridge thus providing communication with the gas source, the detector and the recirculation pump. FIG. 1d provides yet another view of the housing head (300) including ports (307, 308 and 310); the membrane sample (302); the housing bowl (305); and the breaking cylinder (306).

In one embodiment, where the sample is a wetted membrane cartridge, the sample may have a first surface facing outward toward the exterior of the housing and a second surface facing inward toward the hollow tube. Gas may flow under pressure, from the gas source (201) through three way valve (FV220) into the housing through port (307) such that it contacts a first surface of a membrane having a surface facing the exterior of the housing. The gas may permeate through the wetted membrane sample, i.e. to the permeate side of the membrane, and flow through the hollow tube (303) and exit the housing via port (308) in communication with three way valve (FV221), which is in communication with the detector. The gas may enter the detector via a first detector port in communication with three way valve (FV221), and exit the detector via a second detector port which is in communication with the recirculation pump (PU-201). The recirculation pump may be in communication with three way valve (FV222) such that the gas circulates back to the housing and re-enters the housing through port (309) in communication with three way valve (FV 222) and the hollow tube on the permeate side of the sample membrane. The recirculated gas may thus be made available once again to the detector via the pathway described above.

In another embodiment the apparatus may be used to test a porous material, e.g. a membrane cartridge in the reverse orientation as described above, such that the membrane surface described above as the permeate side, now becomes the surface first contacted by the gas and the membrane surface described above as the first surface now becomes the permeate side. The change in orientation is accomplished by altering the flow of gas through a plurality of three way valves. In this embodiment gas will flow under pressure from the gas source through a three valve (FV 220), but will be diverted to a port (308) in communication with the inner portion of the membrane sample. The gas may permeate through the membrane sample into the space between the housing and the sample membrane and will flow out of the housing through a port (310) in communication with three way valve FV 221. Three way valve 221, which is in communication with the detector, transports the gas through a first detector port into the detector. The gas may exit the detector via a second detector port in communication with the recirculation pump PU-201. The gas may enter the recirculation pump via a first port and exit via second port which is in communication with three way valve (FV222) which is in communication with a port situated near the bottom of the housing (FIG. 1a) such that the recirculated gas is delivered back to the permeate side of the membrane, i.e. the membrane side facing the housing wall, such that it is available once again to the detector via the pathway described above.

EXAMPLES

Example 1

Integrity Testing of Porous Materials with Recirculation of Detectable Gas

Porous membranes were integrity tested using an apparatus similar to the one shown in FIG. 1, except that the apparatus was not configured with a plurality of three way valves. The following protocol was used. A membrane cartridge was wetted using an appropriate liquid for the particular type of membrane. The cartridge was installed in the filter housing which was connected to an FTIR sensor, a recirculation pump, a vacuum pump, and a plurality of valves.

The process of testing a cartridge, using a Programmable Logic Controller, pressure tranducers, and automate valves, was as follows:

1. The recirculation pump was turned on and the system was evacuated to below a set vacuum level (pressure sensors PT 203 & 204 below -10 PSIG) using a Venturi vacuum generator (Vaccon, Medfield, Mass.).
2. Recirculation of the permeate side volume was continued for 10 seconds. The FTIR signal was checked to ensure that it was below a setpoint threshold (44 ppmv $C_2F_6$). The FTIR background signal after several clean up cycles was used to determine the set point. If the level was below the threshold and permeate side was to be set at atmosphere, step 4 was implemented; if initial permeate side test pressure was to be under vacuum step 5 was implemented. If the Tracer Gas level (i.e. detectable substance) was above the threshold, step 3 was implemented.
3. Both sides of cartridge were pressurized with nitrogen or compressed air to a set point pressure (1 psig). PT-203 and PT-204 were monitored. When both were above the set point 10 seconds were allowed to elapse, and then Step 1 was repeated.

4. Both sides of the filter were brought up to 0 PSIG (14.696 PSIA) with nitrogen or compressed air. Both PT-203 and PT-204 were monitored. When both reached 0 psig (±) Step 5 was implemented.
5. Tracer Gas was dosed on the upstream side to a partial pressure set point of 15.5 PSIG. When PT-203 indicated that the pressure was at set point, step 6 was immediately implemented. The skilled artisan will also appreciate that while dosing was done instantly, dosing also could have been done using a ramp rate (i.e. psi/second). Ramping may provide several advantages. A slow ramp could potentially allow recognition of a gross defect before putting in the full amount of tracer. It could also provide for a more reproducible set point pressure. Another advantage relates to detecting defects in pleated membranes. Certain defects on the pleat peaks may in some cases get pinched off under high differential pressure—a slow ramp may eliminate this blinding effect
6. The upstream was pressurized to the final set point differential pressure with nitrogen or compressed air. The differential pressure between PT-203 and PT-204 was monitored. When the differential reached the set point, step 7 was implemented. Pressurization was done instantly but could also have been done using a recipe set ramp rate (i.e. psi/second).
7. The FTIR signal versus time was monitored. If any of the following occurred step 8 was implemented, otherwise signal versus time was monitored continually until the set point time elapsed:
a. PT-204 was above recipe overpressure set point which could signify a gross leak;
b. The FTIR signal was above the set point value also signifying a gross leak;
c. The time on the recipe test timer expired. Typically the timer ranged from 60 to 120 seconds.
8. The downstream/permeate side of the filter was evacuated. This included the FTIR sensor and the recirculation pump, which were evacuated to exhaust. PT-204 was monitored and a 20 second timer was set when the pressure is below recipe set point (−10 PSIG).
9. The upstream side of the membrane cartridge was evacuated to exhaust. PT-203 was monitored and 20 second timer was set when pressure was below recipe set point (−10 psig). Proceed to step 10 when timer expires.
10. The upstream side of the membrane cartridge was pressurized with nitrogen or compressed air to recipe set point (30 psig). PT-203 was monitored and a 5 second timer was set when the pressure was above the set point. When the timer was done, step 11 was implemented, unless the clean up cycle counter (recipe set point for number of cycles—was only 1) was complete, then step 12 was performed.
11. The upstream side of the membrane cartridge was evacuated to exhaust. PT-203 was monitored. A 10 second timer was set when the pressure was below the set point (−10 psig). An increment clean up counter was used to keep track of how many cycles of pressurization with carrier gas followed by evacuation was performed. As stated above, in this experiment one cycle was done. When the timer was done, step 10 was repeated.
12. The filter drain valve was opened and vented downstream of the filter. Monitor PT-203 and PT-204 were monitored.

When PT-203 and PT-204 both reached 0 PSIG (±)10 second timer was set. When timer was done the test was complete.

Example 2

Comparison of FTIR Signal in Membrane with Known Defects

Figure 2:
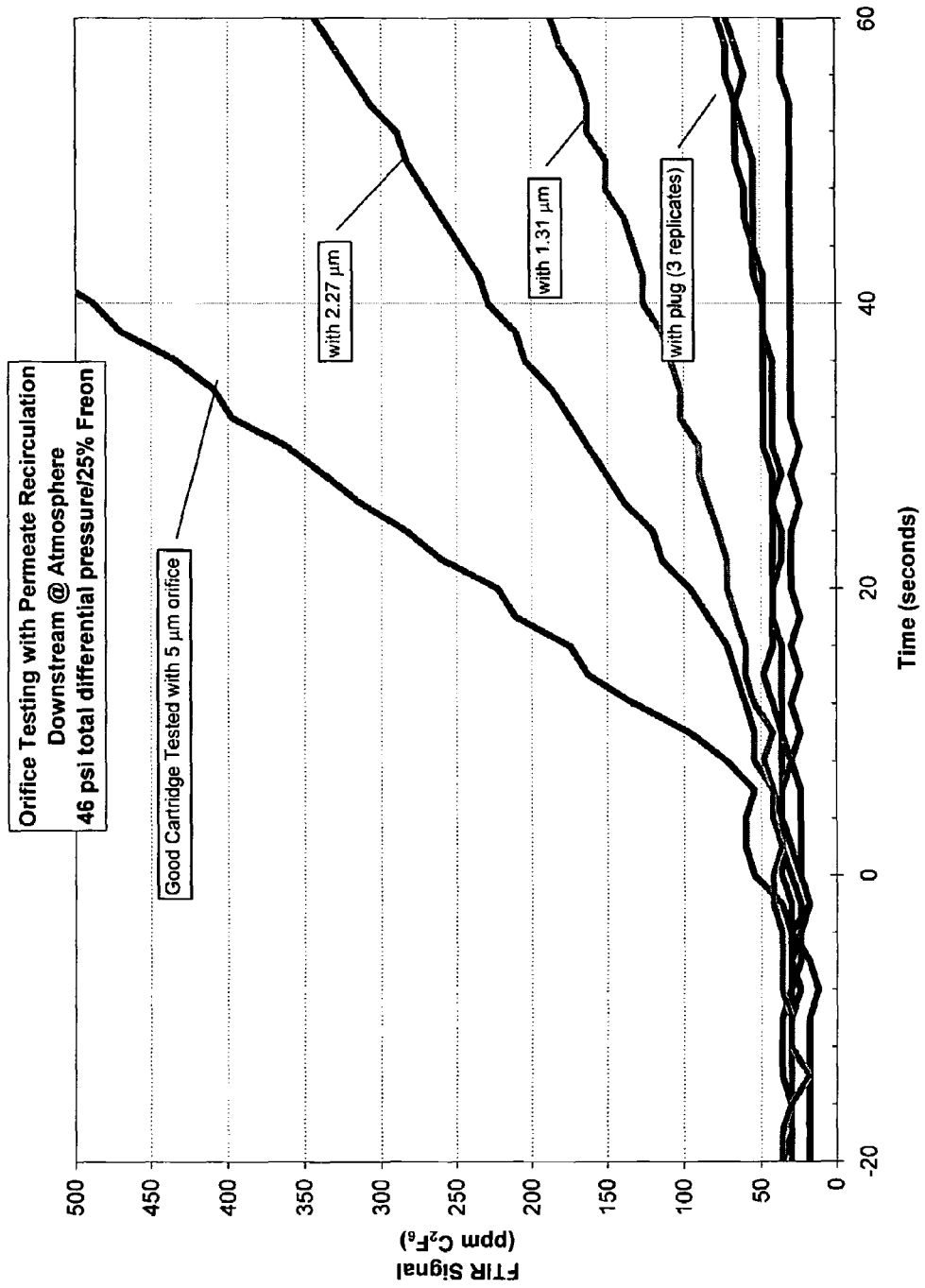
FIG. 2 is a graph showing a comparison of Fourier Transform Infrared Spectroscopy (FTIR) signal in membrane cartridges having different size defects.

Individual good cartridges were tested in conjunction with a series of fixed orifices of a know diameter. To provide a standard for comparison, a plug was inserted in the orifice holder to eliminate the effects of the known defect. A series of tests with the same cartridge were performed with each cartridge tested having a single defect of known diameter. The cartridge used was a 10 inch 0.22 micron hydrophillic PVDF Durapore® (Millipore Corporation, Billerica, Mass.) membrane cartridge subassembly. The results are shown in FIG. 2 and demonstrate distinct curves for defects of differing sizes. The test conditions were 25% (by volume) $C_2F_6$ 75% compressed air, with a trans membrane pressure difference of 46 psi. The unit of time in FIG. 2 is seconds, while the unit for $C_2F_6$ concentration is parts per million (ppm)(by volume). The sensor used is a MKS InDuct FTIR (MKS Instruments, Wilmington, Mass.) with a lower detection limit of 1 ppmv $C_2F_6$.

Figure 3:
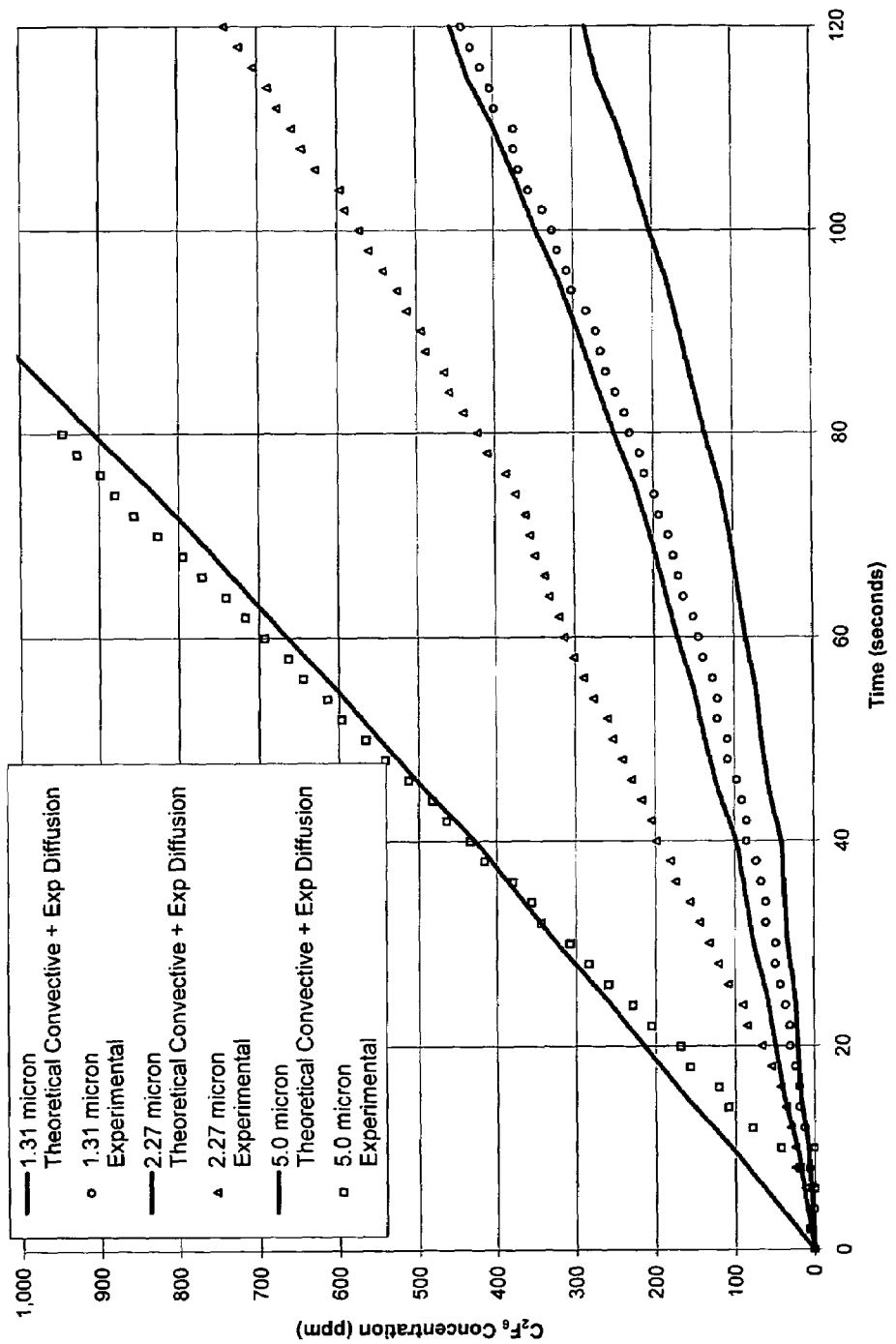
FIG. 3 is graph showing a comparison between theoretically calculated and experimentally observed permeate concentration for membrane cartridges having a defect of known size.

A theoretical concentration of $C_2F_6$ versus time was also calculated assuming choke flow for individual membranes having a defect of known size. FIG. 3 shows a comparison of the calculated values and the experimental results obtained using fixed orifice defects.

Example 3

Integrity Testing of Process Sub-Assembly Cartridges

Figure 4A:
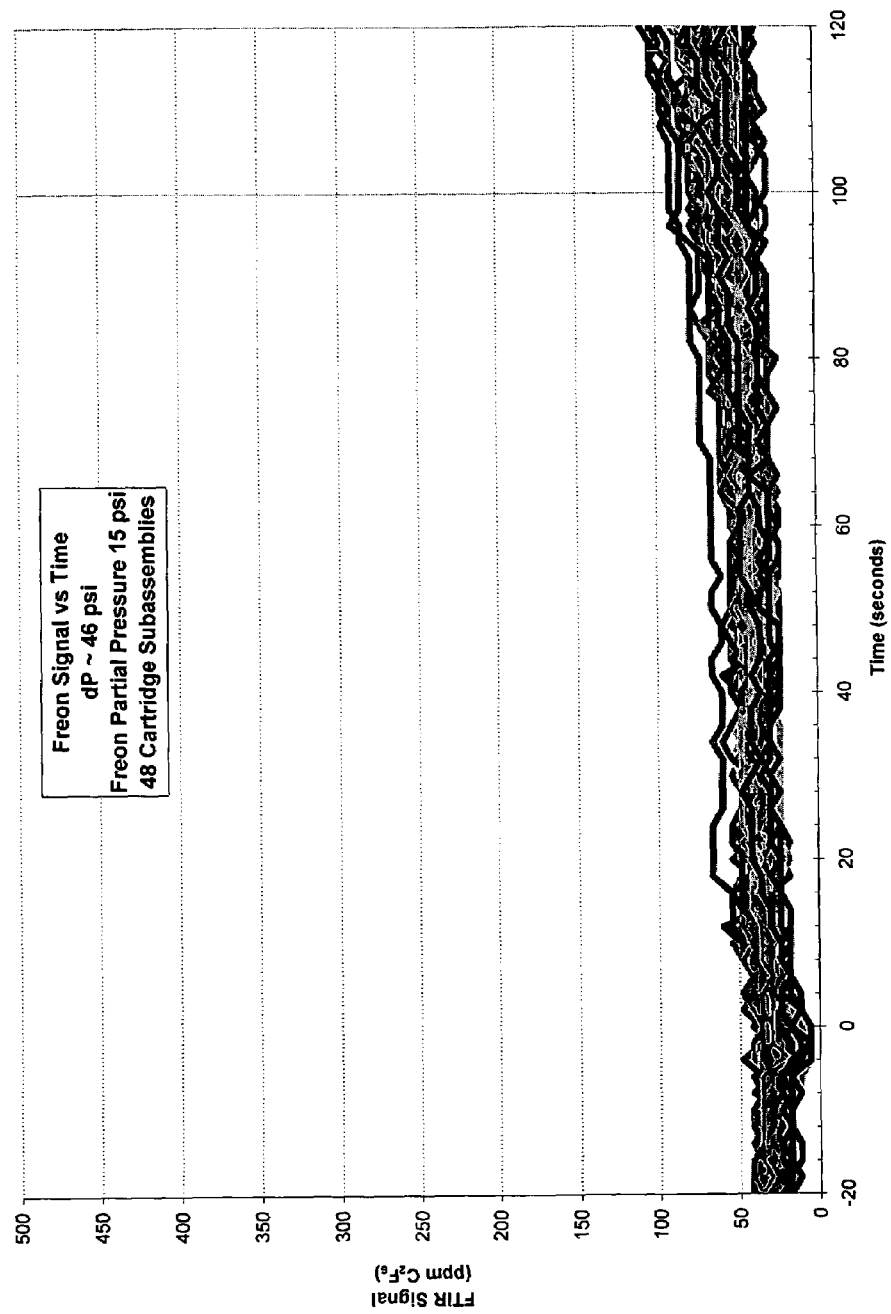
FIG. 4a is a graph showing Freon signal versus time for a sampling of in process membrane sub assemblies.
Figure 4B:
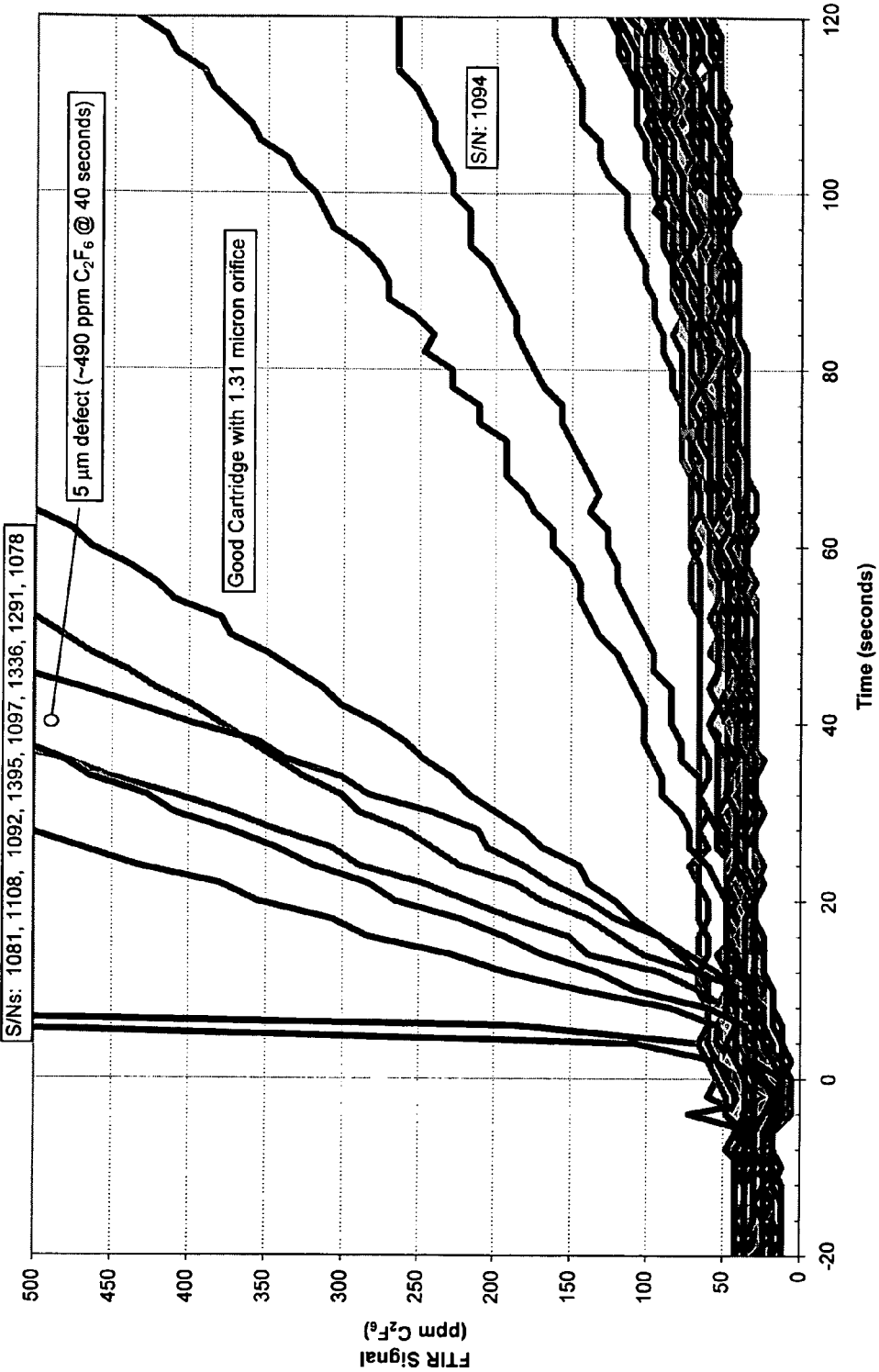
FIG. 4b is a graph showing Freon signal versus time for the same population of membranes described in 4a after further processing.

Integrity testing was performed on 48 production units of 10" process sub assembly cartridges with a 0.22 micron hydrophillic PVDF Durapore® (Millipore Corporation, Billerica, Mass.) membrane. The units were tested both prior to and post gamma irradiation. The test conditions were as reported above in Example 2. The results are shown in FIGS. 4a (pre gamma irradiation) and 4b (post gamma irradiation). After integrity testing using FTIR detection, according to one embodiment of the invention, the same units were subjected to testing with PLATO (photo acoustic detection) (U.S. Pat. No. 5,581,017), and an existing production mass flowrate test (diffusion test) (*Millipore Catalog* 94-95, Millipore Corporation, Billerica Mass.). A functional bacterial retention test was also performed. A comparison of these results is shown in Table 1. ("?" indicates an indeterminate result). The results from FIG. 4b (a known good cartridge with a 1.31 micron defect) was considered as the cutoff for a defective membrane. The integrity test described herein demonstrated good sensitivity under the conditions tested.

TABLE 1

| | FTIR Results: | | | | |
|---|---|---|---|---|---|
| Cartridge ID | Time to reach 245 ppm $C_2F_6$ (seconds) | Slope (ppm $C_2F_6$/ second) | PLATO | Freon Diffusion (sccm) | Retention Results (counts) |
| 1081 | 5 | 86.7 | BAD | DK | TNTC |
| 1108 | 7 | 107 | BAD | DK | TNTC |

TABLE 1-continued

FTIR Results:

| Cartridge ID | Time to reach 245 ppm $C_2F_6$ (seconds) | Slope (ppm $C_2F_6$/ second) | PLATO | Freon Diffusion (sccm) | Retention Results (counts) |
|---|---|---|---|---|---|
| 1092 | 15 | 18.9 | BAD | 0.58 | TNTC |
| 1395 | 20 | 13.8 | BAD | 0.57 | TNTC |
| 1097 | 22 | 17.1 | BAD | 0.9 | TNTC |
| 1336 | 31 | 14.3 | BAD | 0.47 | TNTC |
| 1291 | 27 | 9.8 | BAD | 0.39 | TNTC |
| 1078 | 35 | 8.7 | ? | 0.33 | TNTC |
| 1094 | 109 | 2.2 | GOOD | 0.19 | 3, 4 |
| 1088 | >120 | 0.38 | GOOD | 0.15 | 0 |
| 1103 | >120 | 0.14 | GOOD | 0.16 | 0 |
| 1407 | >120 | 0.24 | GOOD | 0.23 | 0 |
| 1196 | >120 | 0.28 | GOOD | 0.29 | 0 |
| 1181 | >120 | 0.51 | GOOD | 0.3 | 0 |
| 1109 | >120 | 0.35 | GOOD | 0.17 | 0 |
| 1349 | >120 | 0.31 | GOOD | 0.29 | 0 |
| 1293 | >120 | 0.17 | GOOD | 0.17 | NOT TESTED |
| 1398 | >120 | 0.34 | GOOD | 0.21 | |
| 1360 | >120 | 0.25 | GOOD | 0.24 | |
| 1373 | >120 | 0.35 | GOOD | 0.33 | |
| 1191 | >120 | 0.38 | GOOD | 0.23 | |

The cut off for a detective membrane using an existing production mass flowrate lest was 0.47 standard cubic centimeters per minute (sccm).

Example 4

Reproducibility of Integrity Test Results

Figure 5:
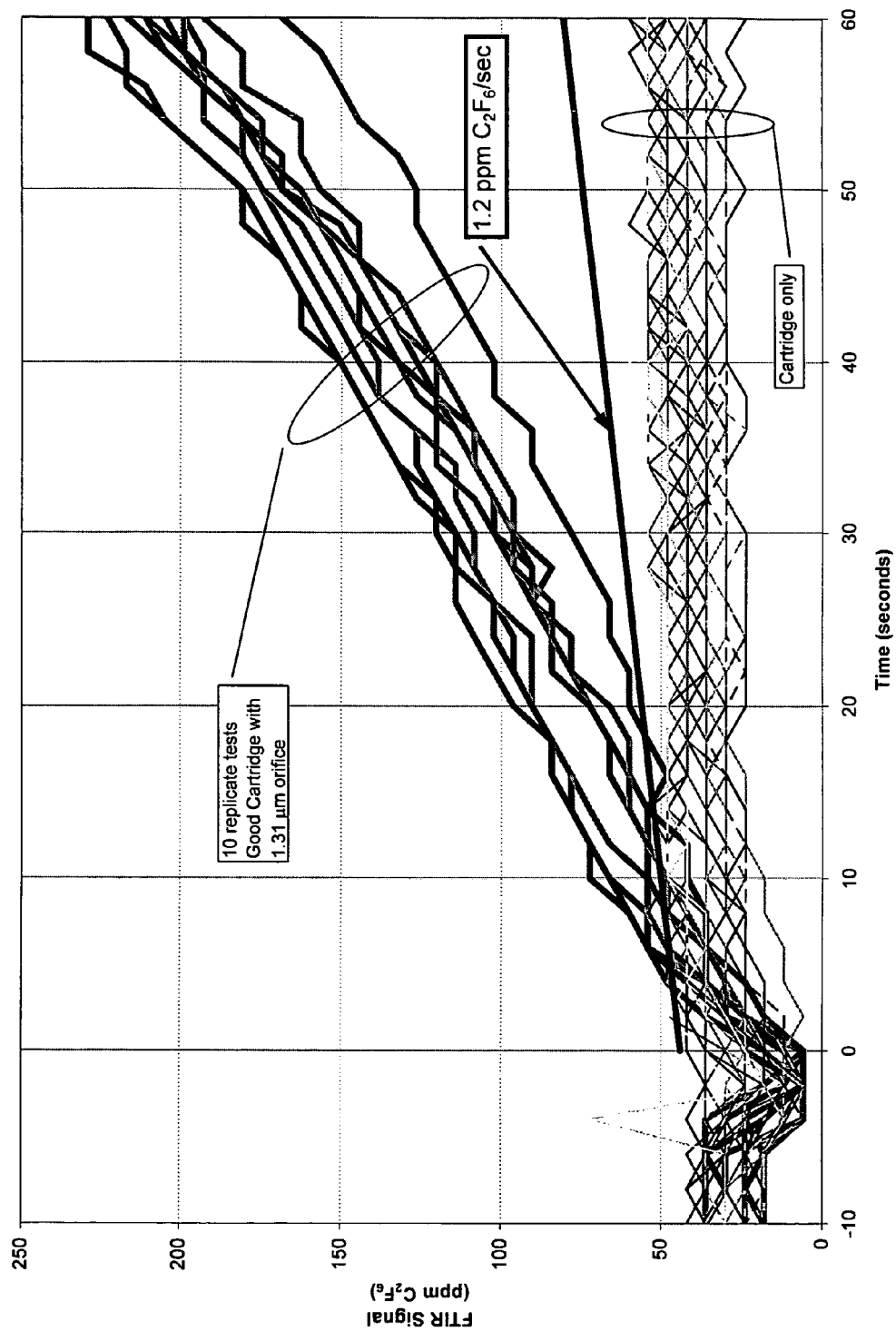
FIG. 5 is a graph showing the results of ten replicate tests of a known good cartridge installed with a 1.31 micron fixed orifice defect versus results for the same cartridge before creation of the defect.

In order to demonstrate that the integrity test described herein provides reproducible results replicate tests were performed on a known good membrane cartridge tested as is or with a fixed orifice defect of known size. The cartridge was comprised of a PVDF Durapore® membrane (Millipore Corp., Billerica, Mass.) and test conditions included using Freon (15.5 psi) as the detectable substance. The system was operated at a pressure differential of 46 psid. FIG. 5 shows the results of 10 replicate tests of a known good cartridge having a deliberately placed 1.31 micron orifice defect. The measured FTIR signal slope of the ten runs has an average of 2.90 ppmv $C_2F_6$/sec) with a standard deviation of 0.20 ppmv $C_2F_6$/sec. For comparison, multiple runs with the same filter alone (no defect) are shown for comparison.

Example 5

Integrity Testing of Asymmetric Membranes

Figure 6:
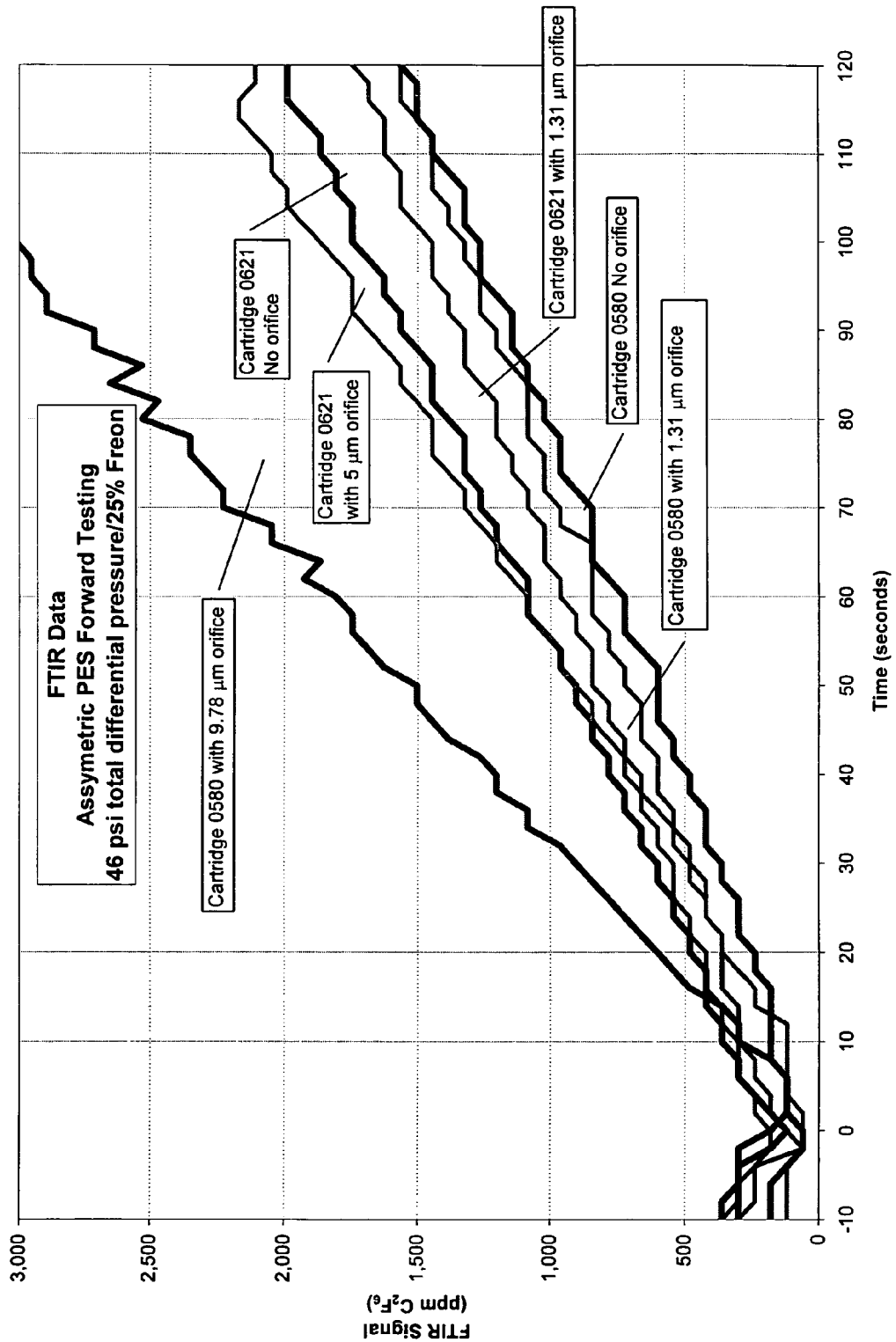
FIG. 6 is a graph showing the results of an integrity test on several asymmetric PES membrane cartridges under non-optimized conditions (forward) (15.5 psig partial pressure of freon and a total contact side (i.e. non-permeate side) pressure of 46 psig). Orifice refers to a fixed defect of known size. Cartridge 0620, although not having a created orifice, was a known defective cartridge.
Figure 7:
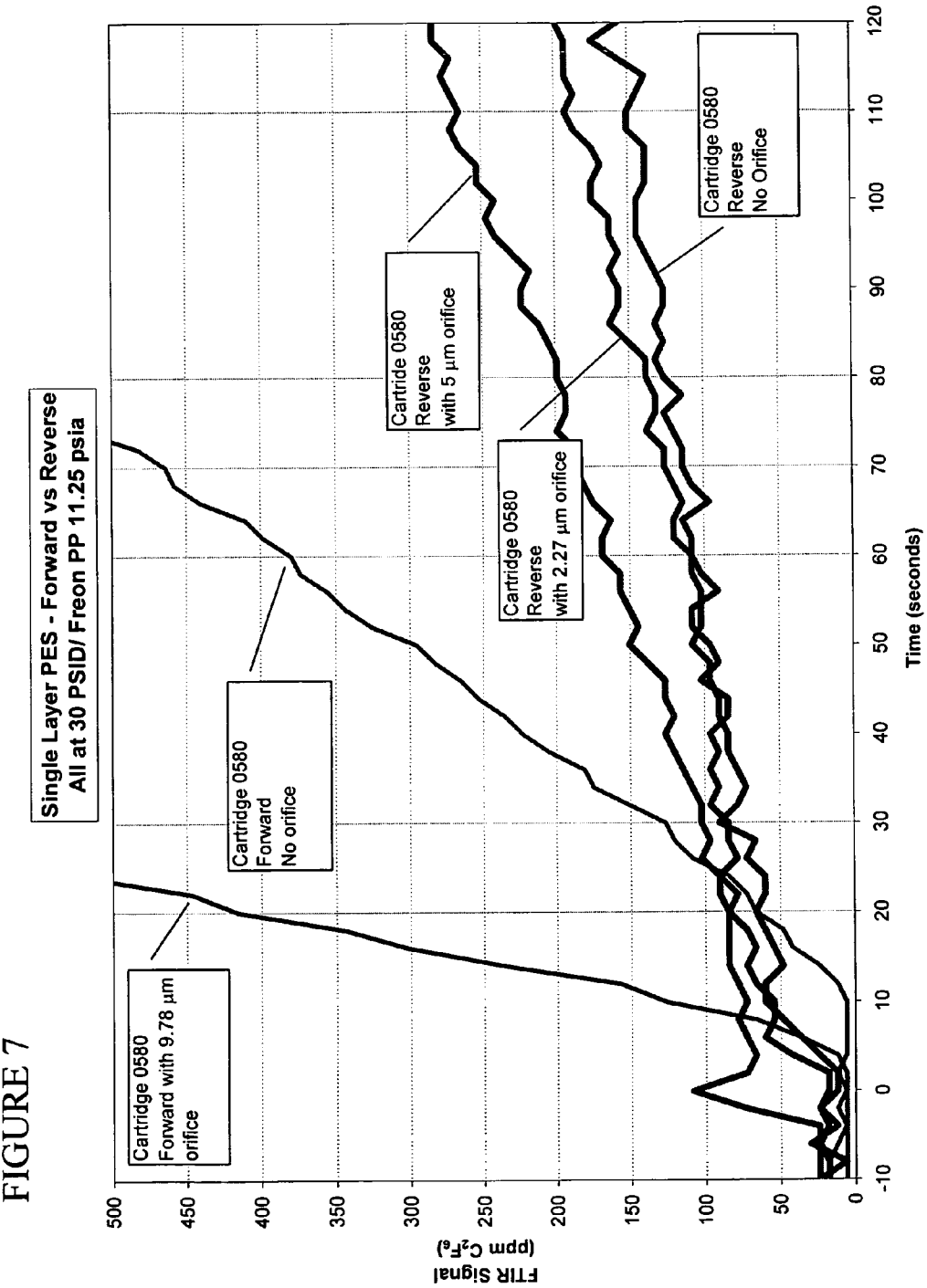
FIG. 7 is a graph comparing results of an integrity test of some asymmetric PES membrane cartridges from FIG. 6 run under optimized (reverse) and non-optimized (forward) conditions( a freon partial pressure of 11.25 psig and a total contact side (i.e. non-permeate side) pressure of 30 psig). Orifice refers to a fixed defect of known size.

Asymmetric membranes were integrity tested according to one embodiment of the invention. It was discovered that the test sensitivity may in some cases be affected by the background diffusion of the tracer gas through the integral membrane. Thus, different membranes may have different optimal test conditions (including gas/vapor mixtures) and limits of detection. FIGS. 6 and 7, show the results obtained when devices containing a thin, asymmetric membrane were tested with various size orifices (i.e. intentionally placed defects). When these membranes were tested using the conditions developed for the Gamma Durapore® (100 to 150 micron thick symmetric structure), the limit of detection was somewhere between 5 and 10 microns. When the test was performed in the reverse direction such that the gas mixture contacted the tight side of the membrane first, (to minimize water layer thinning of the asymmetric structure) and at a lower differential pressure (30 psig vs 46 psig), the detection limit was lowered to between 2 and 5 microns.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated indicated by the following claims

What is claimed is:

1. A method of assessing the integrity of a porous material without allowing the method to reach a steady state comprising a) wetting the porous material with a liquid; b) contacting a first surface of the porous material with a mixture comprising a carrier and a detectable substance; c) applying pressure to the first surface of the porous material such that at least some of the carrier and the detectable substance permeate the porous material; d) recirculating the carrier and detectable substance found in a permeate of the porous material in a fixed volume on the permeate side while continuing to apply the pressure of (c); e) assessing the concentration of the detectable substance in the permeate of the porous material over time; and f) comparing the assessed concentration in (e) with the concentration of the detectable substance in a permeate of an integral porous material exposed to the same conditions over time, wherein an assessed concentration in (e) which is greater than the concentration of the detectable substance in a permeate of the integral porous material indicates the porous material is not integral.

2. The method of claim 1, wherein the at least one of the carrier and the detectable substance is a gas.

3. The method of claim 1, wherein both the carrier and the detectable substance are a gas.

4. The method of claim 1, wherein the source of pressure is compressed air.

5. The method of claim 1, wherein the detectable substance is a fluoro-carbon.

6. The method of claim 5, wherein the fluoro-carbon is freon.

7. The method of claim 1, wherein the porous material is a membrane.

8. The method of claim 7, wherein the membrane comprises a material chosen from polyether sulfone, polyamide, nylon, cellulose, polytetrafluoroethylene, polysulfone, polyester, polyvinylidene fluoride, polypropylene, poly (tetrafluoroethylene-co perfluoro(alkyl vinyl ether)), polycarbonate, polyethylene, glass fiber, polycarbonate, ceramic, and metals.

9. The method of claim 1, wherein the porous material is contained in a cartridge.

10. The method of claim 1, wherein assessing the concentration of the detectable substance is performed with a detector.

11. The method of claim 10, wherein the detector is chosen from Fourier Transform Infra-Red Spectroscopy, mass spectroscopy, and gas chromatography.

12. The method of claim 10, wherein the detector is a Fourier Transform Infra-Red Spectroscopy.

13. The method of claim 1, wherein the liquid is comprised of water.

14. The method of claim 7, wherein the membrane is an asymmetric membrane.

15. The method of claim 7, wherein the membrane is chosen from a single layer membrane and a multi-layered membrane

16. A method of assessing the integrity of a porous membrane without allowing the method to reach a steady state comprising a) wetting the porous material membrane with a liquid b) contacting a first surface of the porous material membrane with compressed air; and with a fluoro-carbon such that a mixture is formed comprising the compressed air and the fluoro-carbon; c) applying pressure to the first surface of the porous membrane such that at least some of the compressed air and the fluoro-carbon permeate the porous membrane; d) recirculating the mixture of (b) found in a permeate of the porous membrane in a fixed volume on the permeate side while continuing to apply the pressure of (c); e) assessing the concentration of the fluoro-carbon in the permeate of the porous membrane over time; 4) comparing the assessed concentration in je) with the concentration of the fluoro-carbon in a permeate of an integral porous membrane exposed to the same conditions over time, wherein an. assessed concentration in .Ie) which is greater than the concentration of the fluoro-carbon in a permeate of the integral porous membrane indicates the porous membrane is not integral. and a) comparing the assessed concentration in (e) with the concentration over time of the fluoro-carbon in a permeate of one or more standard porous membranes, wherein each of said one or more standard porous membranes comprises a defect of known size and is submitted to the same test conditions as the sample porous membranes thereby determining the size of the defect.

17. The method of claim 14, wherein the fluoro-carbon is $C_2F_6$.

18. An apparatus for assessing the integrity of a sample porous membrane without allowing the method of assessing the integrity of a sample porous membrane to reach a steady state comprising:

a) a housing suitable for receiving a porous membrane to be integrity tested; b) a source of a detectable substance in fluid communication with the housing; c) a source of a carrier for the detectable substance, in fluid communication with the housing; d) a detector for detecting the detectable substance; e) a recirculation pump in communication with the detector and the housing for containing the porous material membrane; and f) a source of an external force; wherein the method of assessing the integrity of the porous material received in the housing of (a) in the apparatus comprises i) wetting a porous material with a liquid; ii) contacting a first surface of the porous membrane with a mixture comprising a source of a detectable substance of (b) and a source of the carrier of (c) for the detectable substance; iii) applying an external force of pressure of (f) to the first surface of the porous membrane such that at least some of the carrier and the detectable substance permeate the porous membrane; iv) recircuating the carrier and detectable substance found in a permeate of the porous membrane in a fixed volume on the permeate side by the recirculation pump of (e) while continuing to apply the pressure of (iii); vi assessing the concentration of the detectable substance in the permeate of the porous membrane over time using the detector of (d); vi) comparing the assessed concentration in (iii) with the concentration of the detectable substance in a permeate of an integral porous membrane exposed to the same conditions over time, wherein an assessed concentration in (v) which is greater than the concentration of the detectable substance in a permeate of the integral porous membrane indicates the porous membrane is not integral.

* * * * *